(12) United States Patent
Pusa et al.

(10) Patent No.: US 11,229,376 B2
(45) Date of Patent: Jan. 25, 2022

(54) MEDICAL INSTRUMENT FOR MAGNETIC RESONANCE IMAGING GUIDED RADIOTHERAPY

(71) Applicant: KONINKLIJKE PHILIPS N.V., Eindhoven (NL)

(72) Inventors: Jehki Juhani Pusa, Helsinki (FI); Annemaria Halkola, Vantaa (FI); Teemu Niemi, Vantaa (FI)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 632 days.

(21) Appl. No.: 15/962,555

(22) Filed: Apr. 25, 2018

(65) Prior Publication Data
US 2018/0310857 A1    Nov. 1, 2018

(51) Int. Cl.
*A61B 5/055*    (2006.01)
*A61N 5/10*    (2006.01)
(Continued)

(52) U.S. Cl.
CPC .......... *A61B 5/055* (2013.01); *A61N 5/1049* (2013.01); *A61N 5/1067* (2013.01);
(Continued)

(58) Field of Classification Search
CPC .. A61B 5/055; A61B 5/0035; G01R 33/3415; G01R 33/4808; G01R 33/36;
(Continued)

(56) References Cited

U.S. PATENT DOCUMENTS 7,023,209 B2    4/2006  Zhang
8,958,864 B2 *  2/2015  Amies ................. G01R 33/385
                                                         600/411
(Continued)

FOREIGN PATENT DOCUMENTS

JP      2004344327 A    12/2004
RU        2324509 C2    12/2007
(Continued)

OTHER PUBLICATIONS

Bernstein et al "Handbook of MRI Pulse Sequences" 2004, p. 527-531.

*Primary Examiner* — Christopher Koharski
*Assistant Examiner* — Kaitlyn E Selmer
(74) *Attorney, Agent, or Firm* — Sherry Austin

(57) ABSTRACT

A medical instrument for magnetic resonance imaging guided radiotherapy includes a magnetic resonance imaging system for acquiring magnetic resonance data from an imaging zone, a radiation source for emitting X-ray or gamma ray radiation directed at a target zone within the imaging zone, wherein the radiation from the radiation source directed to the target zone passes through a radiation window of the magnetic resonance imaging system. The magnetic resonance imaging system includes at least one radiation transparent electrical transmission line, which is configured for transmitting an electrical signal and which extends through the radiation window, wherein the electrical transmission line is provided by a microstrip comprising a conductor line extending parallel to the ground layer, wherein the conductor line and the ground layer are separated from each other by a dielectric substrate.

20 Claims, 7 Drawing Sheets

(51) Int. Cl.
  *G01R 33/36* (2006.01)
  *G01R 33/34* (2006.01)
  *G01R 33/3415* (2006.01)
  *G01R 33/48* (2006.01)

(52) U.S. Cl.
  CPC ... *G01R 33/34007* (2013.01); *G01R 33/3415* (2013.01); *G01R 33/36* (2013.01); *G01R 33/4808* (2013.01); *A61N 2005/1055* (2013.01); *G01R 33/4812* (2013.01)

(58) Field of Classification Search
  CPC .......... G01R 33/34007; G01R 33/4812; A61N 5/1067; A61N 5/1049; A61N 2005/1055
  See application file for complete search history.

(56) References Cited

U.S. PATENT DOCUMENTS

| | | |
|---|---|---|
| 2006/0273795 A1 | 12/2006 | Rieke et al. |
| 2009/0212774 A1 | 8/2009 | Bosshard et al. |
| 2010/0026303 A1* | 2/2010 | Zhai .................. G01R 33/3635 324/318 |
| 2010/0320391 A1* | 12/2010 | Antonuk ................. G01T 1/208 250/366 |
| 2012/0286786 A1 | 11/2012 | Schellekens et al. |
| 2013/0090549 A1 | 4/2013 | Meltsner |
| 2014/0266206 A1 | 9/2014 | Dempsey et al. |
| 2016/0146911 A1* | 5/2016 | Chmielewski ... G01R 33/34007 600/411 |
| 2016/0213949 A1 | 7/2016 | Uhlemann |
| 2017/0115369 A1* | 4/2017 | De Weerdt ......... G01R 33/4818 |
| 2017/0361128 A1 | 12/2017 | Lachaine |

FOREIGN PATENT DOCUMENTS

| | | |
|---|---|---|
| WO | 2015135825 A1 | 9/2015 |
| WO | 2016034364 A1 | 3/2016 |

\* cited by examiner

MEDICAL INSTRUMENT FOR MAGNETIC RESONANCE IMAGING GUIDED RADIOTHERAPY

CROSS REFERENCE TO PRIOR APPLICATIONS

This application claims priority to JP 2017-087797 filed Apr. 27, 2017, which is incorporated herein by reference.

FIELD OF THE INVENTION

The invention relates to a medical instrument for radiotherapy, in particular to a transmission line used in the medical instrument.

BACKGROUND OF THE INVENTION

Radiation therapy or radiotherapy is a type of cancer treatment, where the purpose is to kill malignant cells with ionizing, high-energy radiation from a radiation source. Magnetic resonance imaging (MRI) is a medical imaging technique that enables to image the anatomy of a human body. MRI-guided radiotherapy means the use of MRI images to improve the radiation treatment deliveries. To be compatible with the radiation source, the components of the MRI system should be able to withstand the effects of the ionized, high-energy radiation and at the same time should cause as little attenuation as possible of the respective radiation. In particular for the so called radiation window, i.e. the area of the MRI system through which the radiation from the source passes through in order to reach its target, i.e. malignant cells, there is a need for components of the MRI system, which are able to withstand the effects of the radiation and cause little attenuation.

SUMMARY OF THE INVENTION

Various embodiments provide for a medical instrument as described by the subject matter of the independent claim.

In one aspect, the invention relates to a medical instrument for magnetic resonance imaging guided radiotherapy. The medical instrument comprises a magnetic resonance imaging system for acquiring magnetic resonance data from an imaging zone. The medical instrument further comprises a radiation source for emitting X-ray or gamma ray radiation directed at a target zone within the imaging zone. The radiation from the radiation source directed to the target zone passes through a radiation window of the magnetic resonance imaging system.

The magnetic resonance imaging system comprises at least one radiation transparent electrical transmission line. The electrical transmission line is configured for transmitting an electrical signal and extends through the radiation window. The electrical transmission line is provided by a microstrip comprising a conductor line extending parallel to the ground layer. The conductor line and the ground layer are separated from each other by a dielectric substrate.

In another aspect, the microstrip is a multiconductor microstrip and comprises a plurality of conductor lines extending parallel to the ground layer. The ground layer is a common ground layer for the conductor lines separated from the conductor lines by the dielectric substrate.

In another aspect, the position of the transmission line within the radiation window is located at a position of a minimal coupling of the transmission line with one or more receiving coil elements of the magnetic resonance imaging system.

In another aspect, the microstrip is connected to a coil element of an antenna array comprising a plurality of receiving coil elements of the magnetic resonance imaging system and the microstrip is configured for transmitting an RF-signal received by the receiving coil elements of the antenna array through the radiation window.

BRIEF DESCRIPTION OF THE DRAWINGS

In the following preferred embodiments of the invention will be described, by way of example only, and with reference to the drawings in which.

DETAILED DESCRIPTION OF THE EMBODIMENTS

Figure 1:
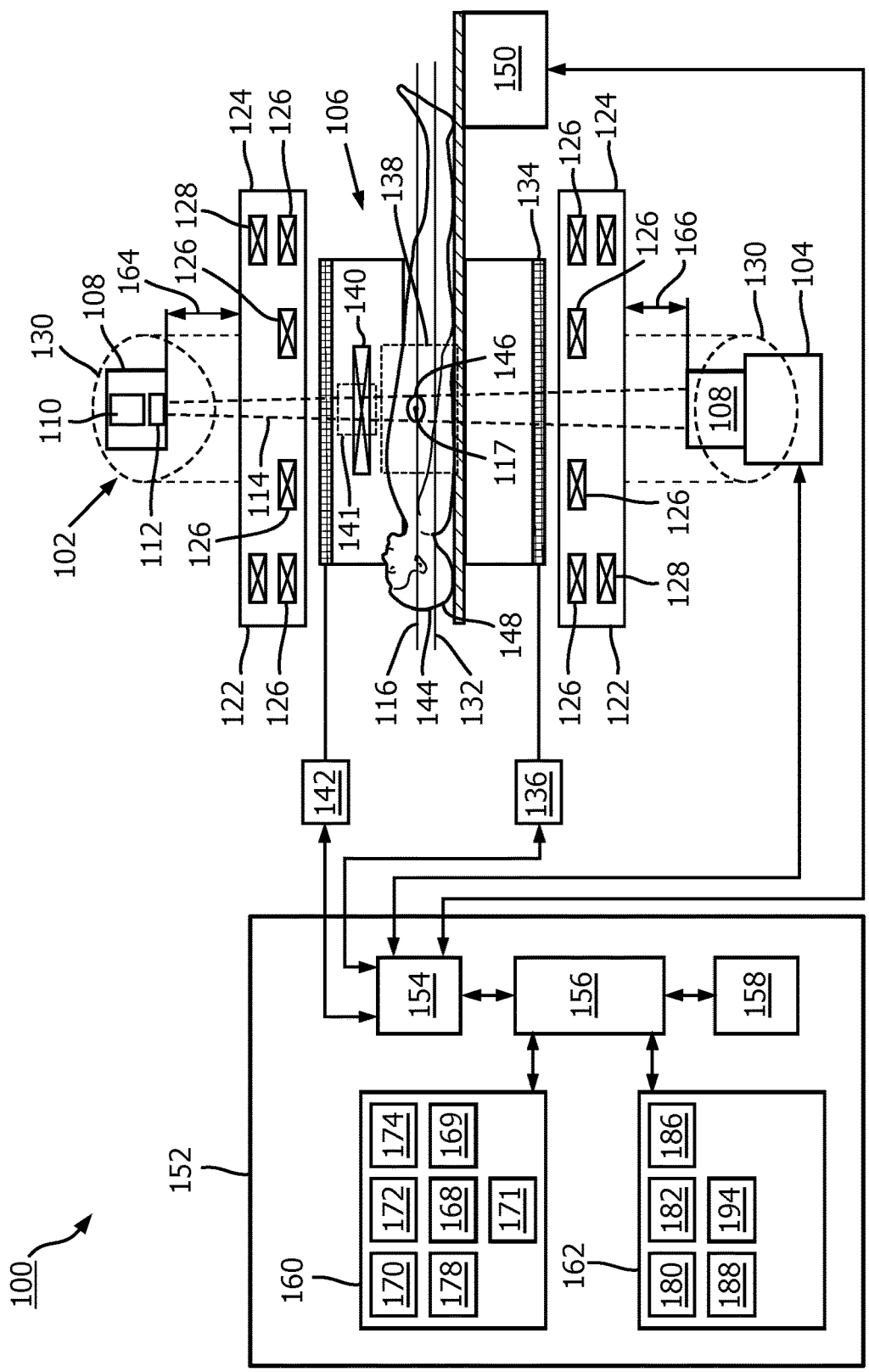
FIG. 1 shows a schematic diagram of an exemplary medical instrument for magnetic resonance imaging guided radiotherapy.

In the following, like numbered elements in the figures are either similar elements or perform an equivalent function. Elements which have been discussed previously will not necessarily be discussed in later figures if the function is equivalent.

Various structures, systems and devices are schematically depicted in the figures for purposes of explanation only and so as to not obscure the present invention with details that are well known to those skilled in the art. Nevertheless, the attached figures are included to describe and explain illustrative examples of the disclosed subject matter.

Radiotherapy is intended to kill malignant cells, while causing minimal harm to surrounding, healthy organs. The total dose required to kill a tumor, which typically is about 20 Gy to 80 Gy, is in general distributed over multiple treatment sessions.

There are two major drawbacks to be taken into account in using a radiation source for radiotherapy: the effects of the radiation on healthy tissue and the uncertainties about the location and shape of the tumor. These drawbacks establish limitations restricting the maximum radiation dose of the treatment.

Exposure to the radiation of the healthy cells surrounding a tumor may be limited by radiating the tumor from different angles and by modifying the beam shape. During a single session, further only a dose of about 2 Gy may be applied. This way healthy cells have some time to recover from the radiation before the next treatment session.

To be able to use these techniques, accurate knowledge of the tumor shape and position is required. In order to image the anatomy comprising the tumor to be treated as well as the healthy tissue surrounding the tumor, MRI may be used. The impact of the aforementioned limitations may be reduced and/or minimized by using image guided radiotherapy, e.g. based on MRI. MR-RT system refers to a magnetic resonance imaging system combined with an external radiation source for radiotherapy.

Magnetic resonance imaging is a medical imaging technique, which may be used both in the diagnosis and as a part of treatment of different diseases such as cancer. Regarding treatment of diseases, MRI may be used for monitoring and guiding of the treatment. For acquiring MRI images, the patient is located within a strong static magnetic field ($B_0$). Then a radio frequency (RF) pulse is applied to the patient. The RF pulse causes the body to emit another RF-signal, the so called nuclear magnetic resonance (NMR) signal, in response. The NMR signal is received with a receive coil and transmitted to a processor which reconstructs an image using the acquired MRI data.

Applying a static magnetic field to a subject containing protons in the imaging zone of the MRI system results in a precession of the protons about the external magnetic field with the Larmor frequency. The Larmor frequency $f_0=(\gamma/2\pi) B_0$, where $\gamma$ is the gyromagnetic ratio and $B_0$ the strength of the external magnetic field. For hydrogen nuclei $\gamma=267.522 \cdot 10^6$ 1/Ts. Thus, with e.g. $B_0=1.5$ T, the Larmor frequency is $f_0 \approx 63.87$ MHz.

Initially the protons precessing about the external $B_0$-field are out of phase and result in no net component. When a strong, e.g. on the order of $10^3$ Watts, RF pulse at the Larmor frequency is applied to the protons, the protons begin precessing in phase with each other. When the RF pulse ceases, the protons emit their excess energy and return to their initial state. The emitted signal is the NMR signal, which is received by receiving coils. The magnitude of the signal is e.g. on the order of $10^{-12}$ Watts and decays exponentially.

MRI may provide a superior soft-tissue contrast compared to other medical imaging techniques such as computed tomography imaging. MRI-guided radiotherapy refers to the use of MRI images to improve the radiation treatment deliveries. The possibility to use MRI images as a guidance in dose delivery planning increases the accuracy of the therapy and potentially improves the treatment outcome. While the number of diagnosed cancers keeps increasing, there is a growing need for more efficient radiation treatments. Increased accuracy of MRI-guided therapy compared to traditional radiation therapy enables the use of higher radiation doses which decreases the needed treatment session times. For MRI-guided radiotherapy a medical instrument may be used, which integrates an MRI system and a radiation source, like e.g. a linear accelerator (LINAC), used to generate the high-energy radiation. An alternative radiation source may e.g. be provided using $^{60}CO$ radionuclides. Such a medical instrument for MRI-guided radiotherapy may be used to deliver accurate radiation therapy treatments for patients with cancer.

The area, where the radiation from the radiation source passes through the MRI-system, in particular through the receiving coils, is called a radiation window or sometimes green zone.

Usually, coaxial cables are used in medical instruments for radiotherapy, because of their good isolation to the surrounding environment. However, coaxial cables are disadvantageous because of two reasons: the amount of metal in these cables with a relatively large diameter attenuates radiation and the round shape of the cable disperses the radiation.

Embodiments may have the beneficial effect, that they allow transmitting an electrical signal through the radiation window using a transmission line provided by a microstrip or a multiconductor microstrip. A multiconductor microstrip allows to transmit multiple electrical signals via the same transmission line. The microstrip may be compatible with the radiation source, due to its radiation resistance and its radiation transparency, i.e. its small attenuation of radiation passing through the microstrip. Transparency refers to the physical property of allowing radiation to pass (at least to a certain fraction) through a material. According to embodiments the microstrips and/or their components have a rectangular cross section, which may reduce the dispersion of radiation. Thus, a transmission line in form of a microstrip in the radiation window may still allow the radiation beam originating from the radiation source to passes through. The transmission line may be used to transmit an RF-signal, e.g., a 63.87 MHz RF-signal, through the radiation window in a receiving coil. In other words, a transmission line provided by a microstrip may work at the Larmor frequency of the MRI system. The possibility to transmit an RF-signal through the radiation window allow for implementing receiving coils with smaller coil elements which yields to a higher signal-to-noise ratio. The materials comprised by the microstrip may be chosen to be non-magnetic in order to not interfere with the MRI data acquisition.

A microstrip may comprise at least one conductor lines. A multiconductor microstrip may comprise a plurality of conductor lines. This may have the beneficial effect, that a plurality of conductor lines can be implemented in a compact arrangement. Furthermore, all the conductor lines can be located at the same position with minimal coupling to other components of the MRI system, like e.g. coil elements.

Microstrips are a type of electrical transmission lines, which may be fabricated using printed circuit board (PCB) technology and may be used to convey microwave-frequency signals. A microstrip comprises one or more conducting strips, also referred to as conductor lines, separated from a common ground plane by a dielectric substrate known as the substrate. Microstrip may entirely be built as pattern of metallization on a substrate.

Signal-to-noise ratio (SNR) is a key feature of any MRI system. SNR is a measure that compares the signal intensity to the image and the noise level. The signal is the average brightness of pixels inside an imaged object relative to the strength of the NMR-signal and noise is the standard deviation of the pixels outside the respective object.

As will be appreciated by one skilled in the art, aspects of the present invention may be embodied as an apparatus or a computer program product. Accordingly, aspects of the present invention may take the form of an entirely hardware embodiment, an entirely software embodiment (including firmware, resident software, micro-code, etc.) or an embodiment combining software and hardware aspects that may all generally be referred to herein as a "circuit," "module" or "system". Furthermore, aspects of the present invention may take the form of a computer program product embodied in one or more computer readable medium(s) having computer executable code embodied thereon.

Any combination of one or more computer readable medium(s) may be utilized. The computer readable medium may be a computer readable signal medium or a computer readable storage medium. A 'computer-readable storage medium' as used herein encompasses any tangible storage medium which may store instructions which are executable by a processor of a computing device. The computer-readable storage medium may be referred to as a computer-readable non-transitory storage medium. The computer-readable storage medium may also be referred to as a tangible computer readable medium. In some embodiments, a computer-readable storage medium may also be able to store data which is able to be accessed by the processor of the computing device. Examples of computer-readable storage media include, but are not limited to: a floppy disk, a magnetic hard disk drive, a solid state hard disk, flash memory, a USB thumb drive, Random Access Memory (RAM), Read Only Memory (ROM), an optical disk, a magneto-optical disk, and the register file of the processor. Examples of optical disks include Compact Disks (CD) and Digital Versatile Disks (DVD), for example CD-ROM, CD-RW, CD-R, DVD-ROM, DVD-RW, or DVD-R disks. The term computer readable-storage medium also refers to various types of recording media capable of being accessed by the computer device via a network or communication link. For example, a data may be retrieved over a modem, over the internet, or over a local area network. Computer executable code embodied on a computer readable medium may be transmitted using any appropriate medium, including but not limited to wireless, wireline, optical fiber cable, RF, etc., or any suitable combination of the foregoing.

A computer readable signal medium may include a propagated data signal with computer executable code embodied therein, for example, in baseband or as part of a carrier wave. Such a propagated signal may take any of a variety of forms, including, but not limited to, electro-magnetic, optical, or any suitable combination thereof. A computer readable signal medium may be any computer readable medium that is not a computer readable storage medium and that can communicate, propagate, or transport a program for use by or in connection with an instruction execution system, apparatus, or device.

'Computer memory' or 'memory' is an example of a computer-readable storage medium. Computer memory is any memory which is directly accessible to a processor. 'Computer storage' or 'storage' is a further example of a computer-readable storage medium. Computer storage is any non-volatile computer-readable storage medium. In some embodiments computer storage may also be computer memory or vice versa.

A 'processor' as used herein encompasses an electronic component which is able to execute a program or machine executable instruction or computer executable code. References to the computing device comprising "a processor" should be interpreted as possibly containing more than one processor or processing core. The processor may for instance be a multi-core processor. A processor may also refer to a collection of processors within a single computer system or distributed amongst multiple computer systems. The term computing device should also be interpreted to possibly refer to a collection or network of computing devices each comprising a processor or processors. The computer executable code may be executed by a plurality processors that may be within the same computing device or which may even be distributed across multiple computing devices.

Computer executable code may comprise machine executable instructions or a program which causes a processor to perform an aspect of the present invention. Computer executable code for carrying out operations for aspects of the present invention may be written in any combination of one or more programming languages, including an object-oriented programming language such as Java, Smalltalk, C++ or the like and conventional procedural programming languages, such as the "C" programming language or similar programming languages and compiled into machine executable instructions. In some instances, the computer executable code may be in the form of a high-level language or in a pre-compiled form and be used in conjunction with an interpreter which generates the machine executable instructions on the fly.

The computer executable code may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider).

Aspects of the present invention are described with reference of block diagrams of apparatus (systems) and computer program products according to embodiments of the invention. It will be understood that each block or a portion of the blocks of the flowchart, illustrations, and/or block diagrams, can be implemented by computer program instructions in form of computer executable code when applicable. It is further understood that, when not mutually exclusive, combinations of blocks in different flowcharts, illustrations, and/or block diagrams may be combined. These computer program instructions may be provided to a processor of a general-purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks.

These computer program instructions may also be stored in a computer readable medium that can direct a computer, other programmable data processing apparatus, or other devices to function in a particular manner, such that the instructions stored in the computer readable medium produce an article of manufacture including instructions which implement the function/act specified in the flowchart and/or block diagram block or blocks.

The computer program instructions may also be loaded onto a computer, other programmable data processing apparatus, or other devices to cause a series of operational steps to be performed on the computer, other programmable apparatus or other devices to produce a computer implemented process such that the instructions which execute on the computer or other programmable apparatus provide processes for implementing the functions/acts specified in the flowchart and/or block diagram block or blocks.

A 'user interface' as used herein is an interface which allows a user or operator to interact with a computer or computer system. A 'user interface' may also be referred to as a 'human interface device.' A user interface may provide information or data to the operator and/or receive information or data from the operator. A user interface may enable input from an operator to be received by the computer and may provide output to the user from the computer. In other words, the user interface may allow an operator to control or manipulate a computer and the user interface may allow the computer to indicate the effects of the operator's control or manipulation. The display of data or information on a display or a graphical user interface is an example of providing information to an operator. The receiving of data through a keyboard, mouse, trackball, touchpad, pointing stick, graphics tablet, joystick, gamepad, webcam, headset, gear sticks, steering wheel, pedals, wired glove, dance pad, remote control, and accelerometer are all examples of user interface components which enable the receiving of information or data from an operator.

A 'hardware interface' as used herein encompasses an interface which enables the processor of a computer system to interact with and/or control an external computing device and/or apparatus. A hardware interface may allow a processor to send control signals or instructions to an external computing device and/or apparatus. A hardware interface may also enable a processor to exchange data with an external computing device and/or apparatus. Examples of a hardware interface include, but are not limited to: a universal serial bus, IEEE 1394 port, parallel port, IEEE 1284 port, serial port, RS-232 port, IEEE-488 port, Bluetooth connection, Wireless local area network connection, TCP/IP connection, Ethernet connection, control voltage interface, MIDI interface, analog input interface, and digital input interface.

A 'display' or 'display device' as used herein encompasses an output device or a user interface adapted for displaying images or data. A display may output visual, audio, and or tactile data. Examples of a display include, but are not limited to: a computer monitor, a television screen, a touch screen, tactile electronic display, Braille screen, Cathode ray tube (CRT), Storage tube, Bistable display, Electronic paper, Vector display, Flat panel display, Vacuum fluorescent display (VF), Light-emitting diode (LED) displays, Electroluminescent display (ELD), Plasma display panels (PDP), Liquid crystal display (LCD), Organic light-emitting diode displays (OLED), a projector, and Head-mounted display.

According to embodiments, the dielectric substrate consists of a radiation resistance material. According to embodiments, the dielectric substrate consists of a material with a total radiation resistance of at least 10 kGy. According to embodiments, the dielectric substrate consists of a material with a total radiation resistance of at least 250 kGy. According to embodiments, the dielectric substrate consists of a material with a total radiation resistance of at least 1 MGy. According to embodiments, the dielectric substrate consists of a material with a total radiation resistance of at least 10 MGy.

Long-term radiation resistance is used to describe materials ability to withstand ionizing radiation. The ionizing high-energy radiation of a radiation source used for radiotherapy, like e.g. a LINAC, may can cause degradation of mechanical and electrical properties of materials in MR-RT components. The higher the radiation resistance of a component the longer the expected lifetime of the component. The 10-years total dose for general MR-LINAC receive coils may, e.g., be estimated as 240 kGy.

Embodiments may have the beneficial effect, that a degeneration of the used materials due to the cumulative lifetime radiation dose, which may lead to malfunctioning of the system as well as to safety problems, may be avoided. Thus, an improved reliability of the system may be achieved. Furthermore, short change or reposition intervals of the respective components may be avoided. Finally, no additional shielding is required. A shielding could, e.g., be implemented with wolfram plates. However, shielding with heavy metals may be disadvantageous, e.g., due to the resulting increase of the component's weight of the component. Furthermore, heavy metals would increase the attenuation of the radiation. For transmission lines passing through a radiation window of a MR-RT system relocation as well as shielding are impractical. However, by choosing an insulator material with a sufficient radiation resistance, the transmission lines may be configured to withstand the effects of radiation.

According to embodiments, the dielectric substrate consists of polyimide. Using polyimide may have the beneficial effect of providing a high radiation resistance. Polyimide may thus resist long-term exposure to high radiation. Polyimide can withstand high-energy radiation up to 10 MGy doses with only negligible or no changes in either its physical or electrical properties. Thinner dielectric substrates cause less radiation attenuation, but they may also cause difficulties in transmission line design. The thickness may be chosen, e.g, to be 101.6 µm. The conductor material was chosen to be copper because of its excellent conductivity.

According to embodiments, the thickness of the conductor lines is minimized. According to embodiments, the thickness of the conductor lines is less than 50 µm. According to embodiments, the thickness of the conductor lines is less than 20 µm. According to embodiments, the thickness of the conductor lines is less than 10 µm.

According to embodiments, the thickness of the ground layer is minimized. According to embodiments, the thickness of the dielectric substrate is minimized. According to embodiments, the thickness of the dielectric substrate is less than 110 µm. According to embodiments, the thickness of the dielectric substrate is less than 50 µm.

In order to reach the patient, the radiation has to travel through the radiation window of the MRI RT system. All system parts located in the radiation window between the radiation source and the patient cause attenuation to the radiation. This attenuation should be minimized, by the design of the components within the radiation window. Further, the attenuation should be as uniform as possible at the radiation window to ensure an even distribution of radiation to the tissue to be treated, e.g. a tumor.

The MRI System comprises at least one receiving coil which provides a sensitive antenna tuned to the Larmor frequency. The oscillating magnetic field of the NMR signal excited by the MRI system induces a small current to the receiving coil. This analog signal is amplified in a low-noise preamplifier of the receiving coil and sent to an analog-to-digital converter, which converts the analog signal into a digital signal. Traditional MRI receiving coils are positioned as close to the imaging zone as possible typically on top and under the patient who lies on a carrier of the MRI system. However, receiving coils used in radiotherapy may not touch the patient, because that might cause shaping of internal organs and tumors.

According to embodiments, the receiving coils are provided by a phased array coil comprising a plurality of coil elements. A phased array coil may comprise e.g. 4 to 32 coil elements. Embodiments may have the beneficial effect, that a phased array coil may acquire magnetic resonance data from large area which is covered by a plurality of coil elements comprised by the phased array coil, while maintaining a high signal-to-noise ratio due to small loops of the individual coil elements. A rule of thumb for the design of the receiving coil is that the highest possible SNR of a circular coil loop is achieved from distance that equals the diameter of a circular loop.

Coupling of neighboring coil elements, which may introduce signals to the coil elements increasing the noise, may be diminished by geometrically overlapping the loops of adjacent coil elements. By overlapping, the neighboring coil elements may be decoupled from each other.

Each coil element may have a preamplifier that amplifies the current induced by the NMR signal. This amplified analog signal is transmitted to an analog-to-digital-converter through a transmission line. As with the coil elements, it may be desirable to minimize the coupling of transmission lines to coil elements as well as to other transmission lines in order to prevent a decrease in the SNR.

According to embodiments, the plurality of receiving coil elements of the magnetic resonance imaging system is arranged in a plurality of parallel rows forming a rectangular matrix structure. The transmission line extents next to a common centerline of coil elements comprised by an outermost column of the matrix structure. Embodiments may have the beneficial effect, that the plurality of receiving coil elements, which are arranged in a matrix structure, may allow parallel imaging along the rows as well as along the columns of the matrix structure. Furthermore, the location of the transmission line next to a common centerline of coil elements comprised by the outermost column may minimize the coupling between the transmission line and the coil elements of the matrix structure.

According to embodiments, the position of the minimal coupling is identified as a position from a set comprising a plurality of positions for which a minimum coupling of the transmission line with the coil elements of the antenna array is measured. The coupling from a transmission line to a receive coil loop may strongly depend on the position of the transmission line. The transmission line may e.g. be moved over the radiation window and the coupling may be measured for different positions. Thus, one or more positions with minimum coupling may be identified.

According to embodiments, the transmission line and at least one of the receiving coil elements of the antenna array are implemented on a common printed circuit board. The substrate of the printed circuit board is used as the dielectric substrate of the microstrip.

Microstrip lines are manufactured on a printed circuit board (PCB). Printed circuit boards mechanically support and electrically connect electronic components using conductive tracks, pads and other features etched e.g. from copper sheets laminated onto a non-conductive substrate. Components, such as capacitors, resistors or active devices, may e.g. be soldered on the PCB or embedded in the substrate. The loops of the receiving coil elements may as well be manufactured on a printed circuit board. It may be beneficial to implement the transmission lines and the loops on the same PCB. Thereby, it may be avoided use two PCB arranged above each other. By using only one common PCB, the thickness of the combination of loop and microstrip may be reduced, e.g. by factor of two According to embodiments, the plurality of electrical transmission lines extends through the radiation window. The plurality of electrical transmission lines is provided by a plurality of microstrips. According to embodiments a plurality of multiconductor microstrips is provided.

According to embodiments, the medical instrument is configured to move the radiation source relative to the radiation window such that the location, where the X-ray or gamma ray radiation directed at the target zone passes through a radiation window, is varied. Embodiments may have the beneficial effect, that a tumor may be irradiated from different angles. In order to not restrict the movement of the radiation source and not restrict the possible angles under which radiation may be applied, it may be necessary to position transmission lines within the radiation window.

According to embodiments, the medical instrument is configured to rotate the radiation source about a rotational axis. According to embodiments, the medical instrument is configured to move the radiation source along the rotational axis.

According to embodiments, the radiation source, like e.g. a LINAC is located on a ring around the MRI system. The LINAC may be rotated over the ring, such that the radiation may be applied from different angles to the patient. Components of the MRI system, such as gradient coils and superconducting coils, may have a radiation window through which the radiation from the radiation source may travel with a minimal attenuation.

According to embodiments, the radiation source is provided by a LINAC emitting X-ray radiation. A linear particle accelerator (LINAC) is a type of particle accelerator. It increases the kinetic energy of charged subatomic particles or ions by subjecting these charged particles to a series of oscillating electric potentials along a linear beamline. LINACs are used for a variety of applications, e.g., they are used for generating X-rays for medicinal purposes in radiotherapy. Linear accelerators are in particular used in radiation treatments for patients with cancer. In radiation treatments, high-energy X-rays generated by the LINAC are used to destroy cancer cells. The radiation is generated by accelerating electrons in a waveguide and colliding the accelerated electrons to a heavy metal target. The collision produces high-energy photons in the Bremsstrahlung process. These photons are directed to the patient's tumor and shaped to conform the shape of the tumor.

According to embodiments, the radiation source comprises radionuclides emitting gamma ray radiation from gamma decays.

Here, X-rays and gamma rays are defined by their origin: X-rays are emitted by electrons, e.g. while being accelerated to produce bremsstrahlung-type radiation, while gamma rays are emitted by a nucleus.

For example, $^{60}CO$ may be used as a radiation source, which emits gamma ray radiation for medical radiotherapy. The so called cobalt therapy or cobalt-60 therapy refers to the medical use of gamma rays from the radioisotope cobalt-60 to treat conditions such as cancer. As used in radiotherapy, cobalt units produce stable, dichromatic beams of 1.17 MeV and 1.33 MeV, resulting in an average beam energy of 1.25 MeV. The cobalt-60 isotope has a half-life of 5.3 years so the cobalt-60 may needs to be replaced occasionally.

According to embodiments, the medical instrument comprises a processor for controlling the medical instrument. The medical instrument further a memory containing machine executable instructions for execution by the processor, wherein execution of the machine executable instructions causes the processor to receive a treatment plan for irradiating the target zone; to acquire the magnetic resonance data using the magnetic resonance imaging system; to reconstruct a magnetic resonance image from the magnetic resonance data; to register a location of the target zone in the magnetic resonance image; to generate control signals in accordance with the location of the target zone and the treatment plan; and to control the radiation source to irradiate the target zone using the control signals.

According to embodiments, the memory further contains pulse sequence data and a parallel magnetic resonance imaging protocol. The pulse sequence data is configured to cause the processor to acquire the magnetic resonance data according to the parallel magnetic resonance imaging protocol. The magnetic resonance image is reconstructed reconstruct from the magnetic resonance data according to the parallel magnetic resonance imaging protocol. Parallel imaging may allow the signal-to-noise ratio (SNR) to be increased, and the image acquisition to be accelerated. Parallel imaging allows artifact-free images to be reconstructed from either aliased images (sensitivity encoding ("SENSE") type reconstruction) or from undersampled data (Generalized autocalibrating partially parallel acquisitions ("GRAPPA") type reconstruction). In a clinical setting a faster image acquisition may, e.g., be used to shorten breath-hold times resulting in fewer motion-corrupted examinations or treatments.

According to embodiments, the memory further contains a set of coil sensitivities for the plurality of receiving coil elements of the antenna array. The parallel magnetic resonance imaging protocol is a SENSE protocol and the magnetic resonance image is reconstructed reconstruct from the magnetic resonance data using the set of coil sensitivities.

Embodiments may have the beneficial effect, that a coil geometry may be applied which allows the use of sensitivity encoding (SENSE), e.g. in head-feet direction of the patient. By using SENSE, the imaging time may be reduced. The acquisition time may be reduced by a factor between one and the number of coil elements used for data acquisition.

A set of independent, decoupled receive coil elements may be used for parallel magnetic resonance acquisition, thereby increasing the signal-to-noise ratio (SNR) compared to a single coil. These single coils of a multi-coil setup in general have better filling factors, i.e. the fraction of the coil detection volume filled with sample is higher, but these coils have non-uniform receive sensitivities and different spatial locations. Thus, the magnetic resonance (MR) signals detectable by the coils are sensitivity encoded giving another and alternative mean in MRI to perform spatial encoding parallel to the usual Fourier signal encoding. Using a set of those coils one can undersample the k-space, i.e. the MRI data space, to accelerate scanning, applying appropriate image reconstruction techniques for reconstructing magnetic resonance images, which are free of under-sampling/unfolding artifacts, and to combine the individual coil images. One example of such an image reconstruction technique that furthermore performs the image combination of images generated with a plurality of coils is the sensitivity encoding or SENSE reconstruction technique. SENSE can also be applied if no under-sampling is performed and yield the optimal image combination in terms of the signal-to-noise ratio.

The SENSE reconstruction technique was introduced by the journal article Pruessmann et al., "SENSE: sensitivity encoding for fast MRI," Magnetic Resonance in Medicine, 42: 952-962 (1999).

The terminology to describe the SENSE reconstruction is well known and has been the subject of many review articles and is present in standard texts on Magnetic Resonance Imaging. For example, "Handbook of MRI Pulse Sequences" by Bernstein et. al., published by Elsevier Academic Press in 2004 contains a re-view of the SENSE reconstruction technique on pages 527 to 531.

FIG. 1 shows a schematic cross-sectional and functional view of a medical instrument 100. The medical instrument 100 is shown as comprising a radiotherapy system 102 and a magnetic resonance imaging system 106. The radiotherapy system 102 comprises a ring mechanism 108. The ring mechanism 108 supports a radiotherapy source 110. The radiotherapy source 110 is representative and may, e.g., be a LINAC X-ray source, an X-ray 2 or a radioisotope gamma radiation source, like a $^{60}CO$ gamma ray source. Adjacent to the radiotherapy source 110 is a multi-leaf beam collimator 112 for collimating a radiation beam 114 that is generated by the radiotherapy source 110. The ring mechanism 108 is also adapted for moving e.g. rotating the radiotherapy source 110 and the beam collimator 112 about a rotational point 117 of the radiotherapy system 102. A rotational axis 116 passes through the rotational point 117.

The magnetic resonance imaging system 106 is shown as comprising a main magnet 122. The ring mechanism 108 is ring-shaped and surrounds the main magnet 122. The main magnet 122 shown in FIG. 1 is a cylindrical type superconducting magnet. However, other magnets are also applicable for embodiments of the invention. The main magnet 122 has a supercooled cryostat 124. Inside the cryostat 124 there is a collection of superconducting coils 126. There are also compensation coils 128 whose current opposes the direction of current in the superconducting coils 126. This creates a low magnetic field zone 130 that circles or encompasses the main magnet 122. The cylindrical main magnet 122 is shown as having an axis 132 of symmetry.

Within the bore of the magnet there is a magnetic field gradient coil 134 which is used for acquisition of magnetic resonance data to spatially encode objects within an imaging zone 138 of the main magnet 122. The magnetic field gradient coil 134 is connected to a magnetic field gradient coil power supply 136. The magnetic field gradient coil 134 is intended to be representative. Typically, magnetic field gradient coils contain three separate sets of coils for spatially encoding in three orthogonal spatial directions. The imaging zone 138 is located in the center of the main magnet 122.

Adjacent to the imaging zone 138 is a radio frequency (RF) coil 140 for manipulating the orientations of magnetic spins within the imaging zone 138 and for receiving radio transmissions from spins also within the imaging zone 138. The radio frequency coil 140 is connected to a radio frequency transceiver 142. The radio frequency coil 140 and radio frequency transceiver 142 may be replaced by separate transmit and receive coils and a separate transmitter and receiver. It is understood that the radio frequency coil 140 and the radio frequency transceiver 142 are simply representative.

According to embodiments, the radio frequency coil 140 may comprise a phased array coil for receiving RF-signals. The radiation beam 114 passes through the magnetic resonance imaging system 106. The radiation beam 114 in particular passes through the radio frequency coil 140. The area of the radio frequency coil 140, through which the radiation beam 114 may pass is defined by the radiation window 141. Through the radiation window 141 extents at least one transmission line of the magnetic resonance imaging system 106, which is provided by a microstrip. According to embodiments, the transmission line transmits an RF-signal received by the radio frequency coil 140 or one of its coil elements, respectively, through the radiation window 141.

Within the center of the main magnet 122 is also located a subject 144. The subject 144 has a target zone (or target zone) 146 and is shown as reposing on a patient carrier 148. The RF coil 140 may transmit RF pulses into the target zone 146. The patient carrier 148 has a mechanical positioning system 150. The mechanical positioning system 150 is adapted for positioning the patient carrier 148 within the main magnet 122. Depending upon the space available inside of the main magnet 122, the mechanical positioning system 150 may move the patient carrier 148 in different directions including a direction perpendicular to the magnet axis 132. If there is more space available inside the main magnet 122 the mechanical positioning system 150 may have more degrees of freedom. For instance, the mechanical positioning system 150 may position the patient carrier 148 with six degrees of freedom.

The radio frequency transceiver 142, the magnetic field gradient coil power supply 136, the mechanical actuator 104, and the mechanical positioning system 150 are all shown as being connected to a hardware interface 154 of a computer system 152. The computer system 152 uses a processor 156 to control the medical instrument 100.

The computer system 152 shown in FIG. 1 is representative. Multiple processors and computer systems may be used to represent the functionality illustrated by this single computer system 152. The computer system 152 comprises the hardware interface 154 which allows the processor 156 to send and receive messages to components of the medical instrument 100. The processor 156 is also connected to a display device 158, computer storage 160, and computer memory 162. The display device 158 may comprise a touch screen sensitive display device. The display device may be provided with a detachable stylus pen to allow a user to more efficiently manipulate the display device 158.

The radiotherapy system 102 is not shown as being connected to the hardware interface 154. The radiotherapy system 102 may be, for example, connected to the hardware interface 154 and communicates with the computer system 152 via the mechanical actuator 104.

For the example shown in FIG. 1, the rotational axis 116 of the radiotherapy system is not coaxial with the magnet axis 132. The rotational point 117 is shown as being off center from the magnet axis 132. It can be seen that the target zone 146 is off-center and away from the magnet axis 132. The radiotherapy system 102 has been moved by mechanical actuator 104 such that the rotational point 117 of the radiotherapy system is within the target zone 146. It can be seen that the ring mechanism 108 has been moved relative to the magnet 122.

The radiation beam 114 passes through the rotational point 117. Placing the rotational point 117 at the center of the target zone 146 allows the target zone to be treated continuously when the radiation beam 114 is created by the radiotherapy source 110 and is rotated by the ring mechanism 108.

Computer storage 160 is shown as containing magnetic resonance data 170 that have been acquired by the magnetic resonance imaging system 106, using pulse sequence data 168 contained by the computer storage 160. The computer storage 160 is shown as further containing magnetic resonance images 172 that have been reconstructed from the magnetic resonance data 170. According to embodiments, the magnetic resonance images 172 are reconstructed according to a parallel magnetic resonance imaging protocol 171. When reconstructing the magnetic resonance images 172 according to the parallel magnetic resonance imaging protocol 171, a set of coil sensitivities 169 contained by the computer storage 160 may be used. The set of coil sensitivities 169 may provide coil sensitivities of a plurality of receiving coil elements comprised by the radio frequency coil 140. The computer storage 160 is shown as further containing a treatment plan 174. The set of coil sensitivities 169 is e.g. used, when the magnetic resonance images 172 are reconstructed according to a SENSE protocol provided by the parallel magnetic resonance imaging protocol 171. The computer storage 160 is shown as further containing radiotherapy control signals 178.

The computer memory 162 contains machine executable instructions 180, 182, 186, 188, 194 for operation by the processor 156. The computer memory 162 is shown as containing a medical instrument control module 180. The medical instrument control module 180 contains machine executable instructions which allow the processor 156 to control the overall functioning of the medical instrument 100. The computer memory 162 is shown as further containing a radiotherapy system control module 182. The radiotherapy system control module 182 contains machine executable instructions which allow the processor 156 to control the functioning of the radiotherapy system 102.

The computer memory 162 is shown as further containing a magnetic resonance imaging control module 186. The magnetic resonance imaging control module 186 contains machine executable code which allows the processor 156 to control the functioning and operation of the magnetic resonance imaging system 106. The computer memory 162 is shown as further containing an image reconstruction module 188. The image reconstruction module 188 contains machine executable code which is used by the processor 156 to transform the magnetic resonance data 170 into images 172.

The computer memory 162 is shown as further containing radiotherapy control signal generation module 194. The radiotherapy control signal generation module 194 contains computer executable code which the processor 156 uses to generate the radiotherapy control signals 178. The radiotherapy control signals 178 may be generated in conjunction with the treatment plan 174.

Figure 2:
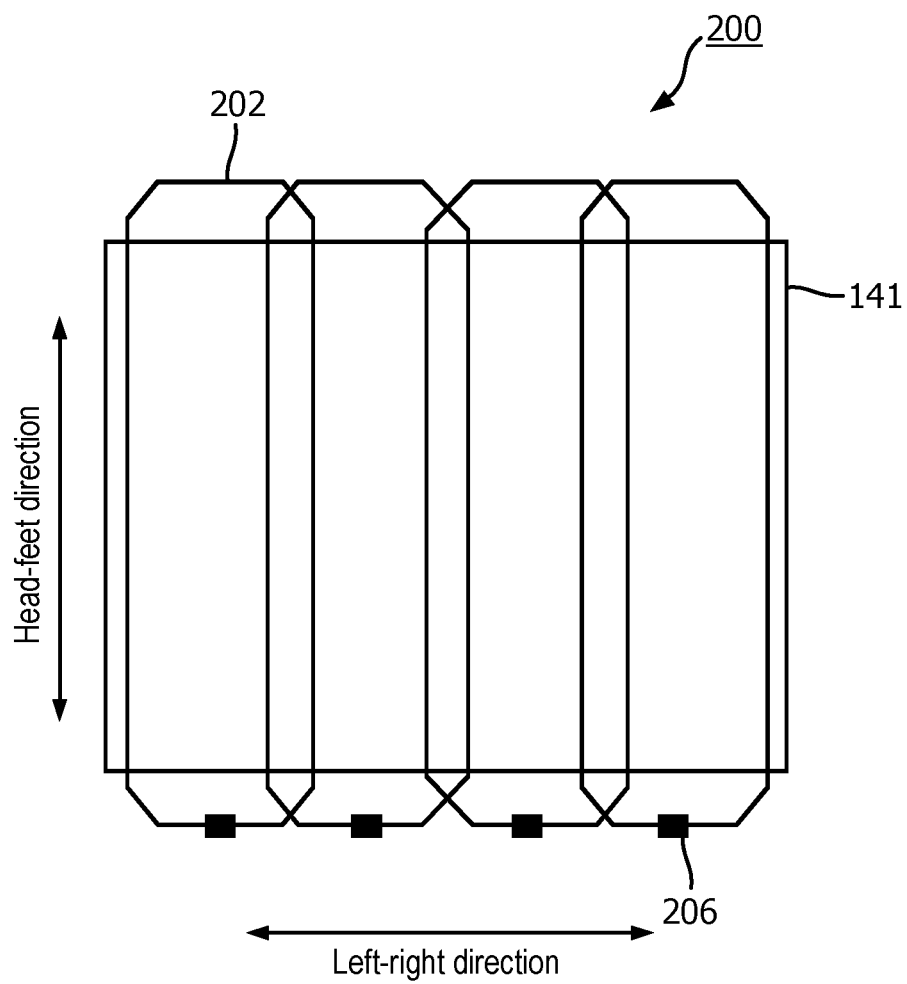
FIG. 2 shows a schematic diagram of a first exemplary phased array coil in the radiation window.

FIG. 2 shows a schematic diagram of a radiation window 141 of a first exemplary phased array coil 200 with four coil elements 202. The phased array coil 200 is for example comprised by the radio frequency coil 140 of FIG. 1. The size of the radiation window 141 is e.g. determined by the maximum rectangular radiation field size used. In the left-right direction the radiation window 141 is required to reach the whole width of the phased array coil 200, since that the radiation can be applied from all directions of the patient's transverse plane. The radiation source may for example be rotatable by 360° around a rotational axis in head-feed direction. Electrical components, like preamplifier 206 for amplifying the RF-signals received by the individual coil elements 202 of the phased array coil 200, are located outside of the radiation window 141, in order to protect the components from the radiation and to avoid an attenuation of the radiation.

Figure 3:
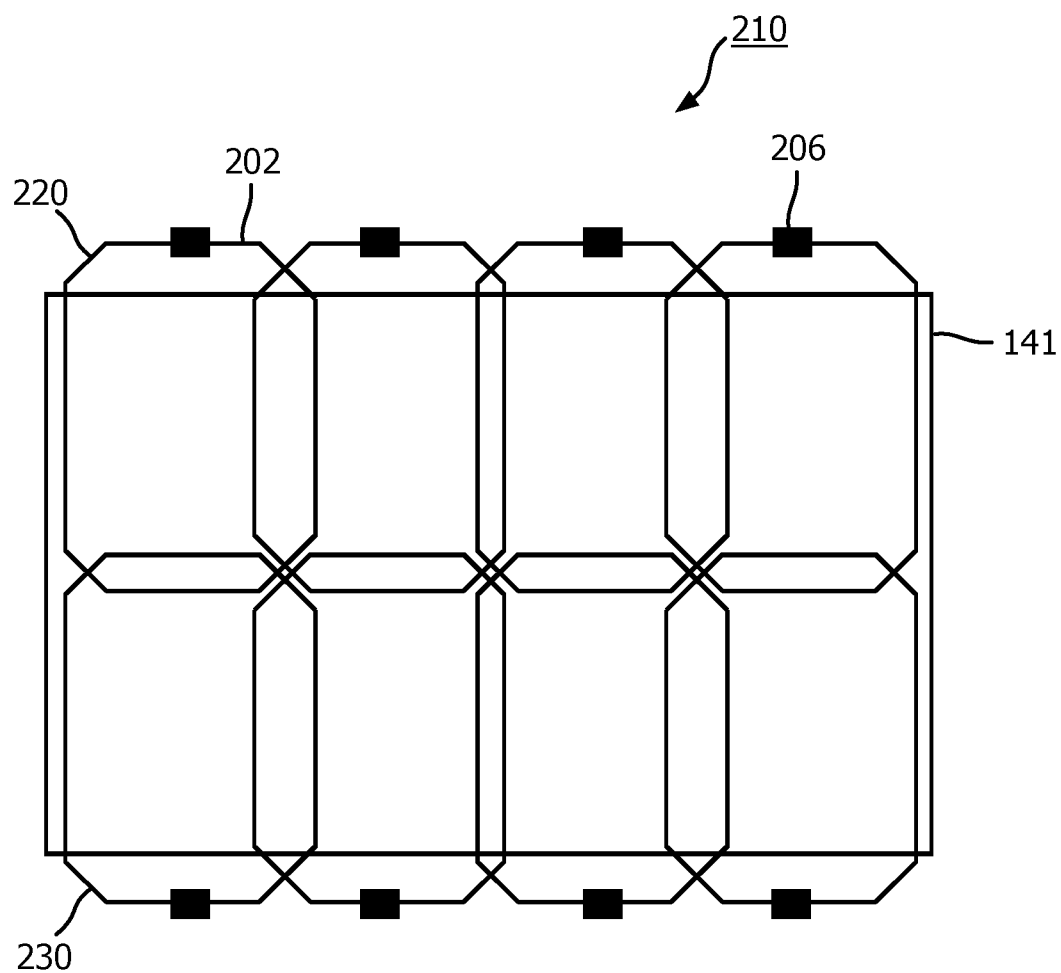
FIG. 3 shows a schematic diagram of a second exemplary phased array coil in the radiation window.

FIG. 3 shows an exemplary geometry of a second phased array coil 210 with smaller coil elements 202 compared to the coil elements of FIG. 2. The phased array coil 210 comprises a plurality of coil elements 202 distributed both in the left-right and in the head-feet direction. The coil elements 202 are arranged in two rows 220, 230. In order to improve the SNR, smaller coil elements 202 with smaller loops may be used. However, this type of coil geometry requires the NMR signal received by the coil elements to be transmitted through the radiation window 141.

To achieve minimal radiation attenuation the radiation window 141 of physical objects, like e.g. coils, should be as thin as mechanically possible and/or made of low-density materials. Furthermore, physical objects, in particular electronic components, such as preamplifiers 206, are moved outside the radiation window 141.

With a coil arrangement, such as in FIG. 2, where all coil elements 202 are in horizontal (left-right) direction SENSE can be used only in horizontal direction. With such a coil arrangement, wherein all coil elements 202 are located in a row, SENSE may only be applied in one direction along the respective row. If images are to be taken in a further direction, e.g. perpendicular to the respective row, one or more additional rows 220, 230 of coil elements parallel to the first row are required. With a coil geometry, such as in FIG. 3, SENSE may be used in head-feet direction reducing the acquisition time by a maximum factor of two. Using plurality of rows, SENSE may in addition be applied in a second direction perpendicular to the first direction. However, when using SENSE in a head-feet direction with a radiotherapy, e.g. LINAC, compatible MRI system, the amplified NMR signal has to be transmitted through the radiation window, such that the RF-signals from all coil elements 202 of both rows 220, 230 can be evaluated a processor of the medical instrument.

Figure 4A:
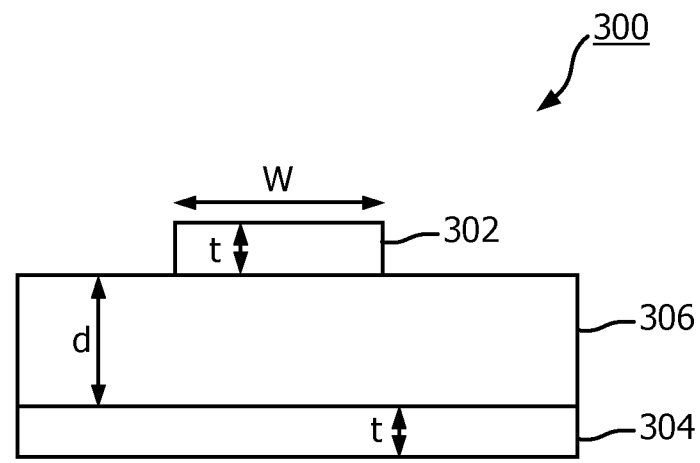
FIG. 4A shows a schematic diagram of an exemplary microstrip.

FIG. 4A shows a schematic diagram of an exemplary microstrip 300. The microstrip 300 comprises a conductor strip 302, which extent parallel to a ground layer 304. The conductor strip 302 and the ground layer 304 are separated from each other by a dielectric substrate 306. The conductor strips 302 for example has a thickness t and a width W. The dielectric substrate 306 for example has a thickness d and the ground layer 304 for example has a thickness t. The effective dielectric constant $\varepsilon_l$ may be calculated as $$\varepsilon_1 = \frac{\varepsilon_r + 1}{2} + \frac{\varepsilon_r - 1}{2} \frac{1}{\sqrt{1 + 12t/W}}.$$

For cases $W/d \geq 1$ the impedance of a microstrip line may be calculated as $$Z_0 = \frac{120\pi}{\sqrt{\varepsilon_1}\left[\frac{W}{d} + 1.393 + 0.667 \ln\left(\frac{W}{d} + 1.444\right)\right]}.$$

The W and d of the microstrip line should be chosen in a way that the above equation gives the wanted impedance, e.g. $Z_0 = 50\Omega$.

Figure 4B:
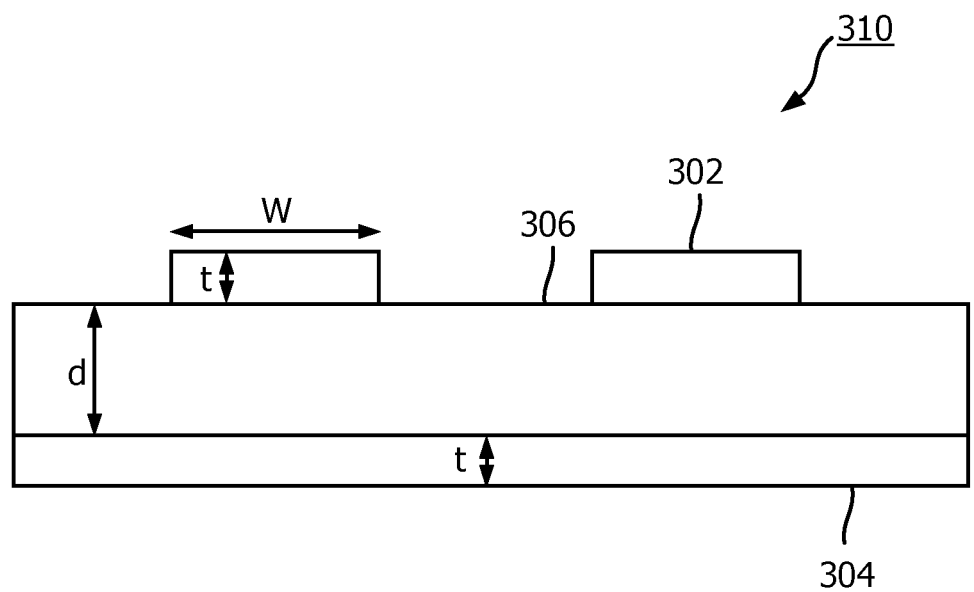
FIG. 4B shows a schematic diagram of an exemplary multiconductor microstrip.

FIG. 4B shows a schematic diagram of an exemplary multiconductor microstrip 310. The multiconductor microstrip 310 corresponds to the microstrip 300 of FIG. 4A, but comprises a plurality of conductor strips 302, e.g. two conductor strips 302, which extent parallel to a common ground layer 304.

The design of an exemplary PCB transmission line provided by a multiconductor microstrip may for example be done with the following specifications: a dielectric substrate made from polyimide with $\varepsilon_r=3.4$ and thickness d=101.6 µm; copper is used as a conductor material, e.g. with a thickness of t=18 µm and a conductivity of $\sigma=5.8 \cdot 10^7$ S/m, a Larmor frequency of $f_0=63.87$ MHz with a 1.5 T MRI system, $Z_0=50\Omega$, length of the transmission line l=35 cm, minimum conductor width=0.1 mm and minimum conductor spacing=0.1 mm.

Figure 5:
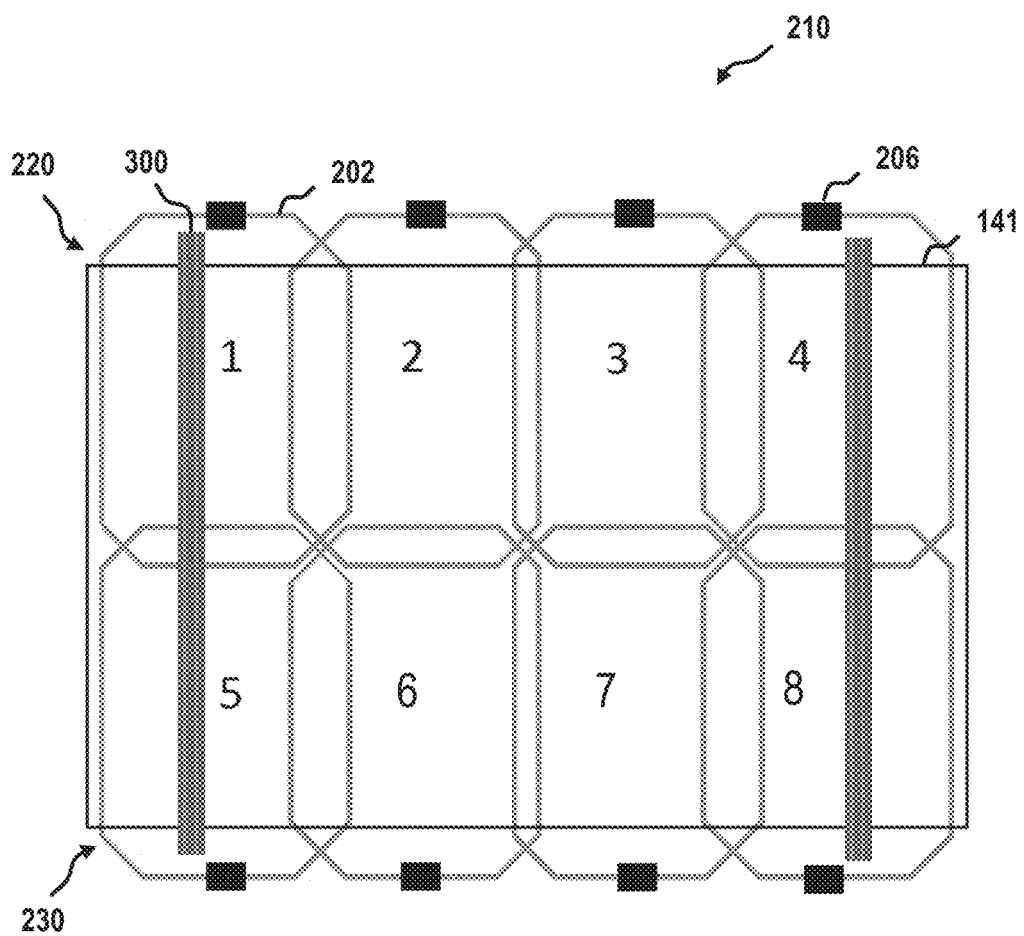
FIG. 5 shows a schematic diagram of the phased array coil of FIG. 3 with multiconductor microstrips of FIG. 4B.

FIG. 5 shows the schematic phase array coil 210 of FIG. 3 with two multiconductor microstrips 300 of FIG. 4. Each multiconductor microstrips 300 comprises two conductor strips and corresponds to two transmission lines. Therefore, each multiconductor microstrips 300 transmits the RF-signal of two coil elements 202 through the radiation window 141. The left multiconductor microstrip 300 transmits for example the amplified RF-signals of the first and second coil element 202 through the radiation window 141, while right multiconductor microstrip 300 transmits the amplified RF-signals of the third and fourth coil element 202.

Before the radiation reaches the patient, it must travel through the MRI system of the MR-RT system. All components of the MRI system located in the radiation window between the radiation source and the patient cause attenuation to the radiation. It is beneficial to use MR-RT components which minimized the attenuation. Furthermore, it may be beneficial that the attenuation is as uniform as possible at the radiation window to ensure an even distribution of radiation to the tissue to be treated, e.g. the tumor.

The attenuation $\alpha$ in percentage is given by $$\alpha = \left(1 - e^{-\frac{\mu}{\rho}\rho t}\right) \cdot 100\%,$$

where $\mu/\rho$ is the mass attenuation coefficient and $x=\rho t$ is the mass thickness given by the product of the thickness t with the density of the material $\rho$.

The mass attenuation coefficient of a material depends on the energy of the radiation. For mixtures and compounds mass attenuation coefficients may be calculated by $$\frac{\mu}{\rho} = \sum_i w_i \left(\frac{\mu}{\rho}\right)_i,$$

where $w_i$ is the fraction by weight of the $i^{th}$ atomic constituent. An accurate estimate for the fraction by weight may be calculated by dividing the sum of protons and neutrons in an atom with a sum of all the protons and neutrons in the molecule.

The microstrip lines may consist of three layers: a common ground layer, a dielectric substrate and one or more conductor lines. The ground layer as well as the conductor may e.g. be made from copper. According to an embodiment, the thickness of the copper layers, i.e. the ground layer and the conductor, is e.g. 18 µm. The dielectric substrate may be made from polyimide (PI) and have a thickness of e.g. 101.6 µm. The density of the copper is $\rho_{Cu}=8.69$ g/cm$^3$. At 2 MeV, the fraction by weight is $$\frac{\mu}{\rho_{Cu}} = 4.205 \cdot 10^{-2} \text{cm}^2/\text{g}.$$

For a thickness of 18 µm the attenuation of copper at 2 MeV is $$\alpha = \left(1 - e^{-4.205 \cdot 10^{-2} \frac{cm^2}{g} \cdot 8.96 \frac{g}{cm^3} \cdot 18 \cdot 10^{-4} cm}\right) \cdot 100\% \approx 0.068\%.$$

The density of PI, i.e. ($C_{20}H_{10}O_5N_2$), is $\rho_{PI}=1.42$ g/cm$^3$. The atomic mass of carbon is 12, 1 of hydrogen, 16 of oxygen and 14 of nitrogen. The total atomic mass of a ($C_{20}H_{10}O_5N_2$) is 358. Therefore, the fraction by weight for the individual atomic constituents of carbon ($w_C$), hydrogen ($W_H$), oxygen ($w_O$), and nitrogen ($W_N$) are:

$$w_C = 12 \cdot \frac{20}{358} = \frac{240}{358}, \ w_H = \frac{10}{358}, \ w_O = \frac{80}{358}, \ w_N = \frac{28}{358}.$$

The mass absorption coefficient for polyimide is $$\frac{\mu}{\rho_{PI}} = \frac{240}{358}\frac{\mu}{\rho_C} + \frac{10}{358}\frac{\mu}{\rho_H} + \frac{80}{358}\frac{\mu}{\rho_O} + \frac{28}{358}\frac{\mu}{\rho_N},$$

which using the mass absorption coefficients for carbon, hydrogen, oxygen and nitrogen known from the literature at 2 MeV gives $$\frac{\mu}{\rho_{PI}} \approx 4.567 \cdot 10^{-2} \frac{cm^2}{g}.$$

The attenuation of 101.6 μm polyimide is $$\alpha = \left(1 - e^{-4.2567 \cdot 10^{-2} \frac{cm^2}{g} \cdot 1.42 \frac{g}{cm^3} \cdot 101.6 \cdot 10^{-4} cm}\right) \cdot 100\% \approx 0.166\%.$$

The total attenuation of the microstrip line with two layers of 18 μm copper as well as 101.6 μm of polyimide is $$\alpha = \left[1 - \left(1 - \frac{0.068}{100}\right)^2 \left(1 - \frac{0.066}{100}\right)\right] \cdot 100\% \approx 0.202\%.$$

Implementing the loops of the coil elements on the same PCB as the multiconductor microstrip line, i.e. providing the polyimide layer by the PCB, no additional substrate layer is needed and attenuation caused by the microstrip line in addition to the attenuation caused by the coil elements is due to the two copper layers:

$$\alpha = \left[1 - \left(1 - \frac{0.068}{100}\right)^2\right] \cdot 100\% \approx 0.136\%$$

Figure 6A:
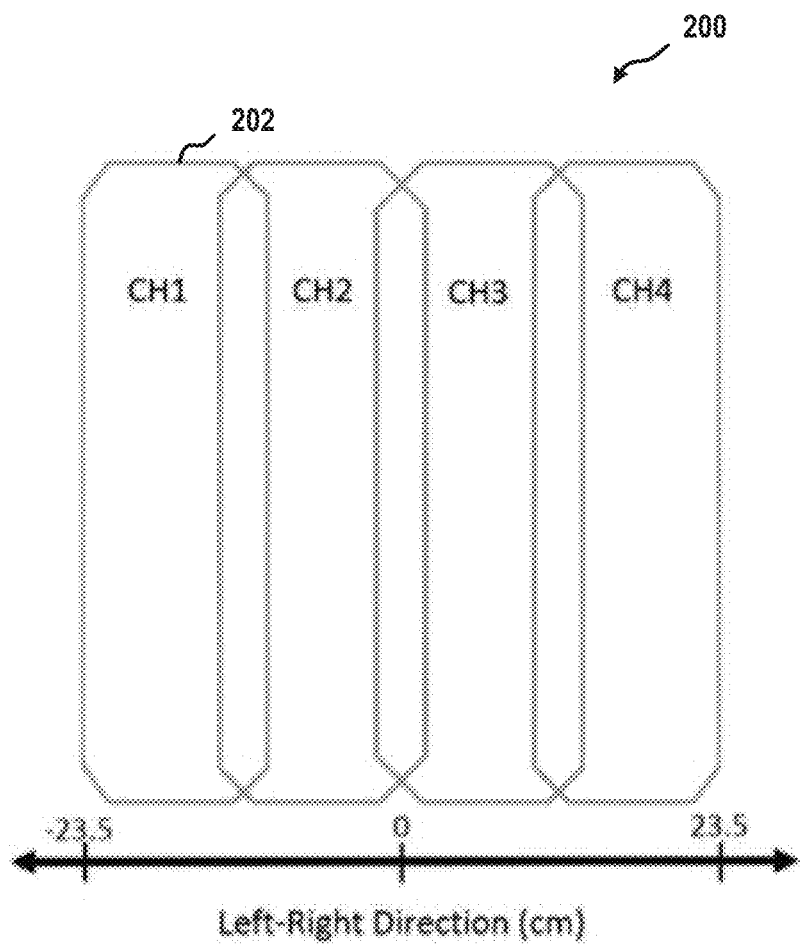
FIG. 6A shows a schematic diagram of a third exemplary phased array coil.

FIG. 6A shows a schematic phased array coil 200 comprising four coil elements 202, each assigned to a signal channel CH1, CH2, CH3, CH4. The phased array coil 200 of FIG. 6A corresponds to the phased array coil 200 of FIG. 2. The neighboring coil elements 202 of phased array coil 200 overlap in order to reduce the coupling between these neighboring coil elements 202. Position 0 cm stands for the center of the phased array coil 200, position–23.5 cm the outer side of channel CH1 and the position 23.5 cm the outer side of channel CH4. Tested cables for measuring the coupling of the coil elements 202 may be aligned in the head-feet direction.

Figure 6B:
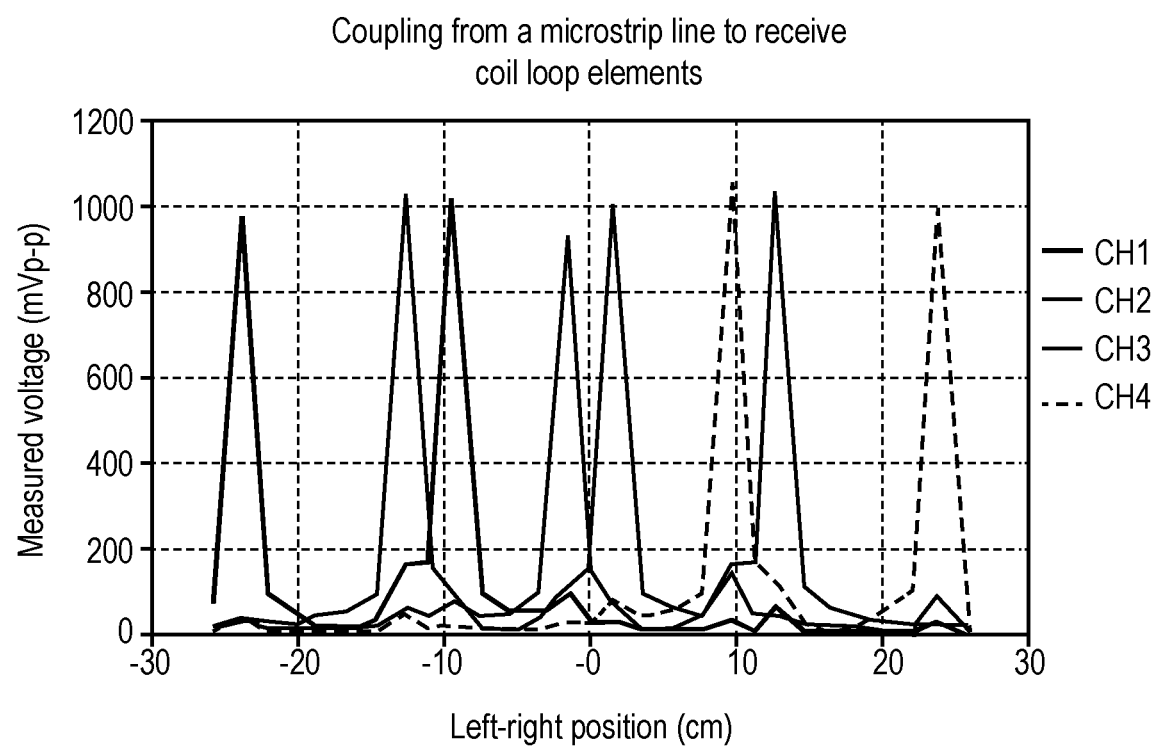
FIG. 6B shows a diagram of the dependence between coupling and position of a microstrip relative to the exemplary phased array coil of FIG. 6A.

FIG. 6B shows a diagram of the coupling of the microstrip line to the four channels depending on the position of the microstrip line. In FIG. 6B exemplary measurement results for a microstrip line comprising a ground plane with width of 6 mm are shown. The optimal positions for the transmission lines are in +18.25 cm and –18.25 cm. The received signals from the first and second coil element 202 may beneficially be transmitted through the loop of the first coil element 202 and the signals from the third and fourth coil element 202 may beneficially be transmitted through the loop of the fourth coil element 202. Using a microstrip line with two top conductors may simplify the transmission of two signals with two adjacent microstrip lines. The microstrip line e.g. consists of two 0.3 mm top conductor strips separated 6 mm away from each other on a 12 mm ground plane. The microstrip line may be implemented on the same substrate as the other PCB transmission lines discussed above in context of FIG. 4 and may e.g. be 35 cm long.

It is understood that one or more of the aforementioned embodiments of the invention may be combined as long as the combined embodiments are not mutually exclusive.

While the invention has been illustrated and described in detail in the drawings and foregoing description, such illustration and description are to be considered illustrative or exemplary and not restrictive; the invention is not limited to the disclosed embodiments.

Other variations to the disclosed embodiments can be understood and effected by those skilled in the art in practicing the claimed invention, from a study of the drawings, the disclosure, and the appended claims. In the claims, the word "comprising" does not exclude other elements or steps, and the indefinite article "a" or "an" does not exclude a plurality. A single processor or other unit may fulfill the functions of several items recited in the claims. The mere fact that certain measures are recited in mutually different dependent claims does not indicate that a combination of these measured cannot be used to advantage. A computer program may be stored/distributed on a suitable medium, such as an optical storage medium or a solid-state medium supplied together with or as part of other hardware, but may also be distributed in other forms, such as via the Internet or other wired or wireless telecommunication systems. Any reference signs in the claims should not be construed as limiting the scope.

What is claimed is:

1. A medical instrument for magnetic resonance imaging guided radiotherapy, the medical instrument comprising:
a magnetic resonance imaging system for acquiring magnetic resonance data from an imaging zone; and
a radiation source for emitting X-ray or gamma ray radiation directed at a target zone within the imaging zone, wherein the radiation from the radiation source directed to the target zone passes through a radiation window of the magnetic resonance imaging system,
wherein the magnetic resonance imaging system comprises at least one radiation transparent electrical transmission line, which is configured for transmitting an electrical signal, and
wherein the radiation transparent electrical transmission line passes through the radiation window from a first end of the radiation window to a second end of the radiation window which is opposite the first end.

2. The medical instrument of claim 1, wherein the at least one radiation transparent electrical transmission line comprises a multiconductor microstrip, wherein the multiconductor microstrip includes a ground layer, and a plurality of conductor lines extending parallel to the ground layer, wherein the ground layer is a common ground layer for the conductor lines, and wherein the common ground layer is separated from the conductor lines by a dielectric substrate.

3. The medical instrument of claim 1, wherein the at least one radiation transparent electrical transmission line comprises a microstrip, wherein the microstrip includes a conductor line and a ground layer, and wherein the ground layer is separated from the conductor line by a dielectric substrate.

4. The medical instrument of claim 3, wherein the thickness of the conductor lines is less than 20 μm.

5. The medical instrument of claim 3, wherein the thickness of the dielectric substrate is less than 110 μm.

6. The medical instrument of claim 5, wherein the thickness of the dielectric substrate is less than 50 µm.

7. The medical instrument of claim 1, wherein the magnetic resonance imaging system includes at least one coil element, and wherein a position of the radiation transparent transmission line within the radiation window is located at a position of a minimal coupling of the transmission line with the at least one coil element of the magnetic resonance imaging system.

8. The medical instrument of claim 7, wherein the magnetic resonance imaging system comprises an antenna array, wherein the at least one coil element comprises a plurality of receiving coil elements, wherein the antenna array comprises the plurality of receiving coil elements, and wherein the receiving coil elements of the antenna array of the magnetic resonance imaging system are arranged in a plurality of parallel rows forming a rectangular matrix structure, wherein the radiation transparent transmission line extends next to a common centerline of coil elements comprised by an outermost column of the matrix structure.

9. The medical instrument of claim 7, wherein the position of the minimal coupling is identified as a position among a plurality of positions, for which a minimum coupling of the radiation transparent transmission line with the coil elements of the antenna array is measured.

10. The medical instrument of claim 1, wherein the magnetic resonance imaging system includes a receiving coil element, and wherein the radiation transparent transmission line is connected to the receiving coil element, and wherein the radiation transparent transmission line is configured for transmitting an RF-signal received by the receiving coil element from the first end of the radiation window to the second end of the radiation window which is opposite the first end.

11. The medical instrument of claim 10, wherein the radiation transparent transmission line and the receiving coil element are implemented on a common printed circuit board.

12. The medical instrument of claim 1, wherein the medical instrument is configured to move the radiation source relative to the radiation window such that a location, where the X-ray or gamma ray radiation directed at the target zone passes through the radiation window, is varied.

13. The medical instrument of claim 1, wherein the radiation source is provided by a linear accelerator emitting X-ray radiation.

14. The medical instrument of claim 1, wherein the radiation source comprises radionuclides emitting gamma ray radiation from gamma decays.

15. The medical instrument of claim 1, wherein the medical instrument further comprises:
a processor for controlling the medical instrument;
a memory containing machine executable instructions for execution by the processor, wherein execution of the machine executable instructions causes the processor to:
receive a treatment plan for irradiating the target zone;
acquire the magnetic resonance data using the magnetic resonance imaging system;
reconstruct a magnetic resonance image from the magnetic resonance data;
register a location of the target zone in the magnetic resonance image;
generate control signals in accordance with the location of the target zone and the treatment plan; and
control the radiation source to irradiate the target zone using the control signals.

16. The medical instrument of claim 15, wherein the memory further contains pulse sequence data and a parallel magnetic resonance imaging protocol, wherein the pulse sequence data is configured to cause the processor to acquire the magnetic resonance data according to the parallel magnetic resonance imaging protocol, wherein the magnetic resonance image is reconstructed reconstruct from the magnetic resonance data according to the parallel magnetic resonance imaging protocol.

17. The medical instrument of claim 16, wherein the magnetic resonance imaging system comprises an antenna array, wherein the at least one coil element comprises a plurality of receiving coil elements, wherein the antenna array comprises the plurality of receiving coil elements, wherein the memory further contains a set of coil sensitivities for the plurality of receiving coil elements of the antenna array, wherein the parallel magnetic resonance imaging protocol is a sensitivity encoder protocol, and wherein the magnetic resonance image is reconstructed from the magnetic resonance data using the set of coil sensitivities.

18. A medical instrument for magnetic resonance imaging guided radiotherapy, the medical instrument comprising:
a magnetic resonance imaging system configured to acquire magnetic resonance data from an imaging zone, wherein the magnetic resonance imaging system includes:
a radiation window,
a coil element disposed within the radiation window,
an amplifier, wherein the amplifier is connected to the coil element and is configured to amplify an RF signal received by the coil element, wherein the amplifier is disposed outside the radiation window, and
at least one radiation transparent electrical transmission line, wherein the radiation transparent electrical transmission line is connected to the amplifier and is configured for transmitting an analog electrical signal from the amplifier disposed outside the radiation window, through the radiation window from a first side of the radiation window to a second side of the radiation window which is opposite the first side; and
a radiation source configured to emit X-ray or gamma ray radiation directed at a target zone within the imaging zone, wherein the radiation from the radiation source directed to the target zone passes through the radiation window of the magnetic resonance imaging system.

19. The medical instrument of claim 18, wherein the magnetic resonance imaging system comprises an analog-to-digital converter, wherein the radiation transparent transmission line is connected to the analog-to-digital converter and is configured to transmit the analog electrical signal from the amplifier through the radiation window from the first side of the radiation window to the second side of the radiation window which is opposite the first side, and to the analog-to-digital converter.

20. The medical instrument of claim 3, wherein the dielectric substrate consists of a material with a total radiation resistance of at least 250 kGy.

* * * * *